United States Patent [19]

Wollensak et al.

[11] 4,219,503

[45] Aug. 26, 1980

[54] PROCESS FOR PRODUCING 2,6-DIALKYLANILINES

[75] Inventors: John C. Wollensak, Bloomfield Hills; Donald H. Lucast, West Bloomfield, both of Mich.

[73] Assignee: Ethyl Corporation, Richmond, Va.

[21] Appl. No.: 63,783

[22] Filed: Aug. 6, 1979

[51] Int. Cl.$^2$ .................... C07C 85/00; C07C 85/20
[52] U.S. Cl. .......................... 260/578; 260/566 R; 260/576; 260/577; 260/690
[58] Field of Search ........... 260/578, 576, 577, 566 R, 260/690

[56] References Cited

U.S. PATENT DOCUMENTS

| | | | |
|---|---|---|---|
| 2,814,646 | 11/1957 | Kolka et al. | 260/577 |
| 3,275,690 | 9/1966 | Stroh et al. | 260/576 |
| 3,923,892 | 12/1975 | Klopfer | 260/578 |
| 4,128,582 | 12/1978 | Governale et al. | 260/578 |

Primary Examiner—John Doll
Attorney, Agent, or Firm—Donald L. Johnson; Robert A. Linn; Joseph D. Odenweller

[57] ABSTRACT

An improved 2,6-dialkylaniline process carried out by reacting an aromatic amine having an unsubstituted ortho position with an olefin in the presence of an aluminum anilide type catalyst followed by catalyst deactivation and distillation to remove 2,6-dialkylaniline. The distillation residue is catalytically hydrogenated and then distilled to recover additional 2,6-dialkylaniline.

24 Claims, No Drawings

PROCESS FOR PRODUCING 2,6-DIALKYLANILINES

BACKGROUND OF THE INVENTION

Aromatic amines having unsubstituted ortho positions can be alkylated in the ortho position by reaction with an aliphatic olefin in the presence of aluminum trianiline (Kolka et al, U.S. Pat. No. 2,814,646). The reaction rate can be promoted by adding a Friedel-Crafts catalyst, e.g. aluminum chloride (Stroh et al, U.S. Pat. No. 3,275,690). Another method of ortho alkylating aromatic amines is to form a catalyst by adding an alkyl aluminum halide, e.g. diethyl aluminum chloride, to the aromatic amine and reacting the mixture with an olefin (Klopfer, U.S. Pat. No. 3,923,892). In another process a hydrogen halide, e.g. hydrogen chloride, is added to the aromatic amine containing an aluminum trianilide catalyst and this is then reacted with an olefin (Governale et al, U.S. Pat. No. 4,128,582). These patents are incorporated herein by reference for their disclosure of methods of ortho alkylating aromatic amines by reaction with an olefin in the presence of an aluminum anilide type catalyst. The present invention is an improvement upon such known procedures whereby yields are increased.

Summary

According to the present invention, 2,6-dialkylanilines are made by (a) reacting an aromatic amine having an unsubstituted ortho position with an olefin in contact with an aluminum anilide type catalyst, (b) deactivating the catalyst, (c) distilling to remove light ends and 2,6-dialkylaniline, (d) catalytically hydrogenating the distillation residue and (e) distilling the hydrogenated residue to obtain additional 2,6-dialkylaniline formed from the hydrogenation.

DESCRIPTION OF THE PREFERRED EMBODIMENTS

A preferred embodiment of the invention is an improvement in a process for making 2,6-dialkylaniline by reacting an aromatic amine, said aromatic amine having at least one nuclear position ortho to an amine group unsubstituted except for hydrogen, and at least one hydrogen atom bonded to the amine groups, with an olefin selected from (a) ethylene when the other nuclear position ortho to said amine group is unsubstituted or substituted with a secondary or tertiary alkyl group containing 3-6 carbon atoms or (b) a $C_{2-6}$ olefin when said other nuclear position ortho to said amine group is substituted with methyl or ethyl, in the presence of an aluminum anilide catalyst, deactivating said aluminum anilide catalyst and distilling the resultant product to recover most of the 2,6-dialkylaniline formed in said process leaving a residual product. The improvement comprises catalytically hydrogenating the residual product to from additional 2,6-dialkylaniline and recovering this additional 2,6-dialkylaniline from the hydrogenated residual product.

Kolka et al, U.S. Pat No. 2,814,646, describes the ortho alkylation of aromatic amines by reaction of an aromatic amine with an olefin in the presence of a catalyst. The catalyst is an aluminum derivative of an aromatic amine. The aromatic amine may be mono- or polynuclear and may have other substituents as long as there is a position on a nuclear benzene ring ortho to an amino group which is available for alkylation and there is at least one hydrogen atom bonded to the amine nitrogen. Examples of suitable starting materials are aniline, amino naphthalene, amino anthracene, o-toluidine, m-toluidine, p-toluidine, o-ethylaniline, o-chloroaniline, p-chloroaniline and the like.

Examples of suitable olefins are ethylene, propylene, butylene, isobutylene, eicosene and the like. The aluminum anilide type catalyst is made by reacting the aromatic amine which must have at least one hydrogen bonded to the amino nitrogen with aluminum metal, aluminum alkyl, aluminum amide and the like. Preferably about 0.1–20 wt % of the aromatic amine is converted to aluminum anilide type catalyst. The alkylation is carried out at elevated temperatures above about 300° C. under olefin pressure. The Kolka et al process is operable at lower temperatures down to about 250° C. and up to decomposition temperature, e.g. 400° C.

Stroh et al, U.S. Pat. No. 3,275,690, is a modification of the above process in which a small amount of a Friedel-Crafts catalyst is used as a promoter. Examples mentioned by Stroh et al are aluminum chloride, aluminum bromide, iron chloride, boron trifluoride, zinc chloride, stannic chloride and the like. Aluminum chloride is preferred. The amount of Friedel-Crafts promoter added is 0.5–10 wt % of the amount of aromatic amine. The alkylation temperature is 150°–400° C. Olefin pressures of about 50–300 atmospheres are used.

Klopfer, U.S. Pat. No. 3,923,892, teaches the ortho alkylation of aromatic amines which have at least one hydrogen atom bonded to the amino nitrogen and have an unsubstituted ortho nuclear position. Representative examples are aniline, o-toluidine, m-toluidine, p-isobutylaniline, p-sec-eicosyl aniline, α-naphthylamine, β-naphthylamine and the like. The catalyst is made by adding an alkyl aluminum halide such as diethyl aluminum chloride or ethyl aluminum sesquichloride to the aromatic amine in an amount which provides about one gram atom of aluminum for each 5–40 gram moles of aromatic amine. Part of the aluminum may be provided by reacting aluminum metal with the aromatic amine. The olefins may be mono- or poly- unsaturated, cyclic or acyclic, terminal or internal. Preferred olefins are acyclic monoolefinic hydrocarbons containing 2–50 carbon atoms, e.g. ethylene.

Governale et al, U.S. Pat. No. 4,128,582, describes the use of hydrogen halide to increase the reaction rate when alkylating an aromatic amine with an olefin using an aluminum anilide catalyst. The aluminum anilide catalyst is made by reacting aluminum metal or aluminum alkyl with the aromatic amine. Preferably, hydrogen chloride is used as the promoter in an amount which provides a halogen:aluminum atom ratio of 0.1–2:1.

The improved procedure can be conducted with any aromatic amine which has at least one hydrogen atom bonded to amino nitrogen which is bonded to a nuclear benzene ring and also has at least one unsubstituted ortho position capable of alkylation. These aromatic amines are adequately described in the background patents. Preferred aromatic amines are aniline and o-toluidine.

The olefins used in the present improvement are somewhat more restricted than those used in the several prior art procedures. When the aromatic amine starting material has both positions ortho to a nuclear amine group unsubstituted except for hydrogen or when one of the ortho positions is unsubstituted except for hydrogen and the other ortho position is substituted with a secondary or tertiary alkyl group, then the olefin used in the alkylation should be ethylene. Examples of such aromatic amines are aniline, 0-isopropylaniline, o-tert-butylaniline, o-sec-butylaniline, o-tert-pentylaniline, o-sec-hexylaniline, p-toluidine, 2-isopropyl-4-methylaniline, 2-tert-butyl-4- methylaniline and the like.

When one of the positions ortho to the nuclear amine group is unsubstituted and the other ortho position is substituted with a methyl or ethyl group, e.g. o-toluidine, o-ethylaniline, and the like, then the olefin alkylating agent can be any aliphatic or alicyclic olefin preferably containing from 2 to about 6 carbon atoms such as ethylene, propylene, butene, isobutene, hexene-1, cyclohexene, cyclopentene and the like.

The catalyst used in the improved process can be any aluminum anilide type catalyst. These catalysts are adequately described in Kolka et al, Stroh et al, Klopfer and Governale et al. They are formed by reacting aluminum metal or an aluminum compound such as aluminum alkyl, alkyl aluminum halide, aluminum hydride, aluminum amide and the like with the aromatic amine. The process may include a promoter such as the Friedel-Crafts promoter of Stroh et al or the hydrogen halide promoter of Governale et al.

The amount of catalyst can vary widely. Usually good results are obtained using an amount of aluminum anilide type catalyst that provides about one gram atom of aluminum per each 7–20 gram moles of aromatic amine. The catalyst can be formed by heating the aromatic amine containing aluminum or aluminum compound to a temperature at which they react to form the catalyst. This can vary from ambient temperature up to about 200° C. or higher. This catalyst formation step is preferably conducted under an inert atmosphere in an autoclave.

Following catalyst formation the autoclave is cooled to below the atmospheric boiling point of its contents and then vented.

The autoclave is then sealed and heated to alkylation temperatures of about 200–400° C. under olefin pressure. Pressures of about 500–3000 psig are usually encountered.

The autoclave is maintained at alkylation temperature as olefin is added as required to maintain pressure. Alkylation is usually complete in about 1–8 hours. The autoclave is then cooled and vented.

The catalyst is then deactivated by known methods. Preferably this is accomplished by adding aqueous base. The preferred method is to wash the alkylation mixture with aqueous caustic and remove the aqueous layer which extracts the aluminum content.

Following this the light ends and ortho alkylated aromatic amine are distilled by known procedures. For example, when aniline is alkylated with ethylene the distillation will remove dissolved ethylene, residual water, unreacted aniline, o-ethylaniline and 2,6-diethylaniline. The distillation is conducted until all or substantially all of the 2,6-dialkylaniline is removed leaving a distillation residue.

In the past this distillation residue was of little value other than as fuel. It has now been found that additional quantities of 2,6-dialkyl aromatic amine can be recovered from this residue by following the present improvement. In the case of diethylaniline the additional recovery can be up to 25% of the weight of the distillation residue.

The additional product recovery is accomplished by catalytically hydrogenating the distillation residue and then distilling additional product formed during the hydrogenation. Preferably the distillation residues from several alkylations are collected until a substantial quantity of residue is on hand. A wide range of known hydrogenation catalysts can be used including the catalytic metals in Group VIII, chromium, vanadium, molybdenum and the like. Examples of such catalysts are Raney nickel, nickel on Kieselguhr, ruthenium, ruthenium oxide, rhodium, palladium, platinum, copper chromite and the like. Best results have been achieved by using a palladium containing catalyst, preferably palladium supported on charcoal. Such catalysts are available commercially. The amount of catalyst can vary widely from about 0.001 to 10% by weight based on the distillation residue.

Hydrogenation pressure can vary over a wide range depending upon catalyst, temperature and the specific distillation residue. The pressure can be readily optimized through a few experiments. Pressures should be high enough to cause the formation of 2,6-dialkyl aromatic amines. A pressure range of about 100–5000 psig can be used.

The hydrogenation is preferably conducted at elevated temperature. The optimum temperature will vary with the catalyst used and the specific distillation residue. A preferred temperature range is about 50°–300° C. More preferably 100°–200° C.

The hydrogenation is conducted for a period long enough to form an economically recoverable amount of 2,6-dialkylaniline. This can usually be achieved in about 4–24 hours. The formation of 2,6-dialkyl aromatic amine can be monitored by periodically withdrawing samples for analysis by methods such as gas chromatography.

It is preferred to use hydrogenation conditions as mild as practical while still being effective. Severe conditions tend to hydrogenate the aromatic nucleus and should be avoided.

The hydrogenation can be conducted continuously using a packed bed hydrogenation catalyst. In this embodiment the distillation residue is passed downward through a packed column under hydrogen pressure. Hydrogen is introduced at the bottom of the column and flows upward. Such operations are well known and are referred to as "trickle bed" hydrogenation.

Following hydrogenation the catalyst, if present, is removed from the hydrogenated residue. This can be accomplished by settling, centrifuging, filtering or a combination of these procedures.

The hydrogenated distillation residue is then distilled to recover the 2,6-dialkyl aromatic amine formed during the hydrogenation. The distillation can be conducted at atmospheric pressure. Preferably reduced pressures are used.

The following example shows a typical prior art alkylation process followed by the present improvement.

EXAMPLE 1

Alkylation

In an autoclave place 200 gms of aniline. Flush with nitrogen and heat to about 90° C. and add 15 gms of diethyl aluminum chloride. Seal and stir about 5 minutes. Vent the autoclave to atmospheric pressure. Seal and heat to about 275° C. and continue stirring while pressurizing to about 1000 psig with ethylene. Continue ethylene feed to maintain about 1000 psig at about 320°

C. After 3 hours cool and vent the autoclave. Wash the reaction product with aqueous caustic to remove catalyst. Transfer the product to a distillation vessel and distill to remove first aniline, next o-ethylaniline and then 2,6-diethylaniline. Bottoms temperature reaches about 290° C. during this distillation. Cool the residual material to obtain an oily product analyzing

| | |
|---|---|
| 2,4,6-triethylaniline | 10.1% |
| diethyl-sec-butylaniline | 3.6%[1] |
| 2-sec-butyl-6-ethylaniline | 22.1% |
| diphenylamine | 5.1% |
| monoethyldiphenylamine | 16.3%[2] |
| N-(2-amino-3-ethyl-α-methylbenzylidene)-2,6-diethylaniline | 28.3% |

[1] 2 isomers
[2] 2 isomers

Hydrogenation

Transfer 20 grams of the distillation residue to a glass-linked rocking autoclave and flush the vapor space with nitrogen. Add 2 grams of carbon supported palladium (5% palladium, 20% water) and flush the autoclave with hydrogen. Seal the autoclave and pressurize to 960 psig with hydrogen. While rocking, heat to 163° C. over 2½ hours. Pressures rise to about 4000 psig. Continue hydrogenation at 4000 psig and 163° C. for 18 hours. Cool the autoclave to 17° C. and vent. Filter the contents through a celite filter bed to remove the catalyst. The filtrate is a pale yellow liquid. At this stage, the filtrate was analyzed by gas chromatography which showed that the N-(2-amino-3-ethyl-α-methylbenzylidene)- 2,6-diethylaniline initially present in the distillation residue had disappeared and that 2,6-diethylaniline had formed. Transfer the hydrogenated distillation residue to a distillation vessel and distill to recover 2,6-diethylaniline at 222° C. 100 mm Hg abs. The recovered 2,6-diethylaniline was about 28 wt % of the initial distillation residue.

As shown in the above example, the component in the distillation residue which is the precursor of the 2,6-diethylaniline is N-(2-amino-3-ethyl-α-methylbenzylidene)-2,6,-diethylaniline which has the structure

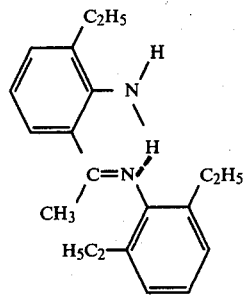

This component appears to have formed during the alkylation through an oxidative coupling of 2,6-diethylaniline. Similar components can form during alkylation of other aromatic amines. The only requirement appears to be that the aromatic amine either before or after alkylation has an ortho alkyl group which was two hydrogen atoms bonded to the α-carbon atom. Using the starting materials described herein, such aromatic amines will form compounds having the following structure

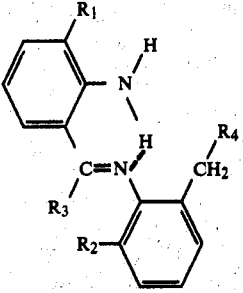

wherein $R_1$ and $R_2$ are lower alkyl groups containing 1 to about 6 carbon atoms and $R_3$ and $R_4$ are hydrogen or methyl. For example, the ortho alkylation of o-toluidine with ethylene using an aluminum anilide type catalyst will form as the main produt, 2-ethyl-6-methylaniline. Distillation of this product will leave a residue containing N-(2-amino-3-methyl-α-methylbenzylidene)-2-ethyl-6-methylaniline according to the chemical path followed by aniline.

Accordingly, a further embodiment of this invention is a process comprising (a) catalytically hydrogenating a compound having the structure

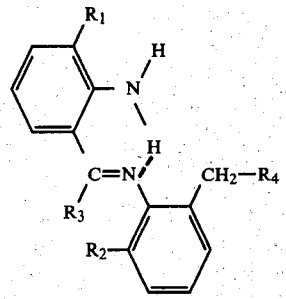

wherein $R_1$ and $R_2$ are lower alkyls containing 1–6 carbon atoms and $R_3$ and $R_4$ are hydrogen or methyl and (b) recovering 2,6-dialkylaniline from the hydrogenated product.

Representative examples of such compounds are:
N-(2-amino-3-isopropylbenzylidene)-2-isopropyl-6-ethylaniline
N-(2-amino-3-sec-butyl-α-methylbenzylidene)-2-sec-butyl- 4-ethylaniline
N-(2-amino-3-isobutyl-α-methylbenzylidene)-2-isobutyl- 6-ethylaniline
N-(2-amino-3-sec-hexyl-α-methylbenzylidene)-2-sec-hexyl-6-ethylaniline The most preferred compound is N-(2-amino-3-ethyl-α-methylbenzylidene)-2,6-diethylaniline which is formed during the aluminum anilide catalyzed alkylation of aniline with ethylene.

The ortho alkylated aromatic amines made by the improved process have many uses. One important use is as an intermediate in the production of pesticides such as those disclosed in U.S. Pat. Nos. 3,853,531; 3,859,308; 3,885,952; 3,888,882; 4,001,325 and 4,025,554.

We claims:

1. In a process for making 2,6-dialkylaniline by reacting an aromatic amine, said aromatic amine having at least one nuclear position ortho to an amine group unsubstituted except for hydrogen, and at least one hydrogen atom bonded to the amine groups, with an olefin selected from (a) ethylene when the other nuclear position ortho to said amine group is unsubstituted or substituted with a secondary or tertiary alkyl group containing 3–6 carbon atoms or (b) a $C_{2-6}$ olefin when said other nuclear position ortho to said amine group is substituted with methyl or ethyl, in the presence of an aluminum anilide catalyst, deactivating said aluminum anilide catalyst and distilling the resultant product to recover most of the 2,6-dialkylaniline formed in said process leaving a residual product, the improvement comprising catalytically hydrogenating said residual product to form additional, 2,6-dialkylaniline and recovering said additional 2,6-dialkylaniline from the hydrogenated residual product.

2. The process of claim 1 wherein said aromatic amine is aniline and said olefin is ethylene.

3. The process of claim 2 wherein said aluminum anilide catalyst is aluminum trianilide.

4. The process of claim 2 wherein said aluminum anilide catalyst is aluminum trianilide to which has been added a Friedel-Crafts promoter.

5. The process of claim 2 wherein said aluminum aniline catalyst is aluminum trianilide to which has been added an HCl promoter.

6. The process of claim 2 wherein said aluminum anilide catalyst is made by adding an alkyl aluminum halide to aniline.

7. The process of claim 6 wherein said alkyl aluminum halide is an alkyl aluminum chloride.

8. The process of claim 7 wherein said alkyl aluminum chloride is diethyl aluminum chloride.

9. The process of claim 7 wherein said alkyl aluminum chloride is ethyl aluminum sesquichloride.

10. The process of claim 2 wherein said catalytically hydrogenating is conducted using a palladium containing catalyst.

11. The process of claim 1 wherein said aromatic amine is o-toluidine and said olefin is ethylene.

12. The process of claim 11 wherein said aluminum anilide catalyst is an aluminum trianilide.

13. The process of claim 11 wherein said aluminum anilide catalyst is an aluminum trianilide to which has been added a Friedel-Crafts promoter.

14. The process of claim 11 wherein said aluminum anilide catalyst is an aluminum trianilide to which has been added an HCl promoter.

15. The process of claim 11 wherein said aluminum anilide catalyst is made by adding an alkyl aluminum halide to aniline or o-toluidine.

16. The process of claim 15 wherein said alkyl aluminum halide is an alkyl aluminum chloride.

17. The process of claim 16 wherein said alkyl aluminum chloride is diethyl aluminum chloride.

18. The process of claim 16 wherein said alkyl aluminum chloride is ethyl aluminum sesquichloride.

19. The process of claim 11 wherein said catalytically hydrogenating is conducted using a palladium containing catalyst.

20. A process for making a 2,6-dialkylaniline, said process comprising (a) catalytically hydrogenating a compound having a structure

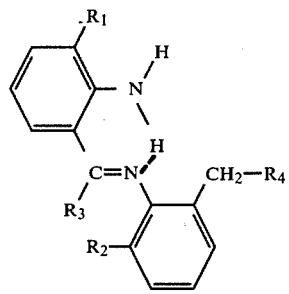

wherein $R_1$ and $R_2$ are lower alkyls containing 1–6 carbon atoms and $R_3$ and $R_4$ are hydrogen or methyl and (b) recovering 2,6-dialkylaniline from the hydrogenated product.

21. The process of claim 20 wherein said compound is N-(2-amino-3-ethyl-α-methyl-benzylidene)-2,6-diethylaniline.

22. The process of claim 21 wherein said catalytically hydrogenating is conducted using a palladium containing catalyst.

23. The process of claim 20 wherein said compound is N-(2-amino-3-methyl-α-methyl-benzylidene)-2-ethyl-6-methylaniline.

24. The process of claim 23 wherein said catalytically hydrogenating is conducted using a palladium containing catalyst.

* * * * *